United States Patent [19]
Chapuis et al.

[11] Patent Number: 5,512,543
[45] Date of Patent: Apr. 30, 1996

[54] USE OF OPTICALLY ACTIVE ISOMERS OF (E)-3,3-DIMETHYL-5-(2,2,3-TRIMETHYL-3-CYCLOPENTEN-1-YL)-4-PENTEN-2-OL AS PERFUMING INGREDIENTS

[75] Inventors: Christian Chapuis, Mies, Switzerland; Antoine Gautier, Lawrenceville, N.J.; Pierre-Alain Blanc, Crassier, Switzerland

[73] Assignee: Firmenich S.A., Geneva, Switzerland

[21] Appl. No.: 284,322

[22] Filed: Aug. 2, 1994

[30] Foreign Application Priority Data

Aug. 17, 1993 [CH] Switzerland ............... 2445-93

[51] Int. Cl.[6] .................................................. A61K 7/46
[52] U.S. Cl. .................. 512/18; 568/836; 568/379; 252/174.11; 252/8.6; 424/76.4; 424/65
[58] Field of Search .............. 512/18; 568/836, 568/379; 252/174.11, 86; 424/76.4, 65

[56] References Cited

U.S. PATENT DOCUMENTS 4,610,813  9/1986  Schulte-Elte et al. .............. 252/522 R

FOREIGN PATENT DOCUMENTS

| | | | |
|---|---|---|---|
| 116903 | 8/1984 | European Pat. Off. | 512/18 |
| 203528 | 9/1985 | European Pat. Off. | 512/18 |
| 466019 | 1/1992 | European Pat. Off. | 512/18 |
| 1922391 | 8/1970 | Germany | 512/18 |
| 2024208 | 1/1980 | United Kingdom | 512/18 |

OTHER PUBLICATIONS

College de France, Paris, Jul. 1961, Laboratoire de Chimie Organique des Hormones, "Principe et applications D'une Nouvelle Methode de Determination Des Configurations Dite Par Dedoublement Partiel", by Alain Horeau.

Chemical Communications, 1971, "Absolute Configuration of Atrovenetin and Related Compounds", by J. S. Brooks and G. A. Morrison.

J. C. S. Perkin 1, 1974, pp. 2114–2119, "Naturally Occurring Compounds Related to Phenalenone. Part VII. Absolute Configuration of Atrovenetin and Related Compounds", by John S. Brooks and George A. Morrison.

*Primary Examiner*—James H. Reamer
*Attorney, Agent, or Firm*—Pennie & Edmonds

[57] ABSTRACT

The chiral isomers of 3,3-dimethyl-5-(2,2,3-trimethyl-3-cyclopenten-1-yl)-4-penten-2-ol and, more particularly, the (−)-(1'R,2S,E)-3,3-dimethyl-5-(2',2',3'-trimethyl-3'-cyclopenten-1'-yl)-4-penten-2-ol and (+)-(1'S,2S,E)-3,3-dimethyl-5-(2',2',3'-trimethyl-3'-cyclopenten-1'-yl)-4-penten-2-ol, are useful as perfuming ingredients to impart sandalwood type odor notes to the perfuming compositions and perfumed articles into which they are incorporated.

15 Claims, No Drawings

1

USE OF OPTICALLY ACTIVE ISOMERS OF (E)-3,3-DIMETHYL-5-(2,2,3-TRIMETHYL-3-CYCLOPENTEN-1-YL)-4-PENTEN-2-OL AS PERFUMING INGREDIENTS

BRIEF SUMMARY OF THE INVENTION

The invention provides novel compounds chosen in the group consisting of:

a. (+)-(1'S,2R,E)-3,3-dimethyl-5-(2',2',3'-trimethyl-3'-cyclolpenten-1' -yl)-4-penten-2-ol;

b. (+)-(1'S,2S,E)-3,3-dimethyl-5-(2',2',3'-trimethyl-3'-cyclopenten-1'-yl)- 4-penten-2-ol;

c. (−)-(1'R,2R,E)-3,3-dimethyl-5-(2',2',3'-trimethyl-3'-cyclopenten-1'-yl)-4-penten-2-ol;

d. (−)-(1'R,2S,E)-3,3-dimethyl-5-(2',2',3'-trimethyl-3'-cyclopenten-1'-yl)- 4-penten-2-ol;

e. (+)-(1'S,E)-3,3-dimethyl-5-(2',2',3'-trimethyl-3'-cyclopenten-1'-yl)-4-penten-2-ol, having an $[\alpha]^{20}_D$ (neat) of about +18.3°; and f. (−)-(1'R,E)-3,3-dimethyl-5-(2',2',3'-trimethyl-3'-cyclopenten-1'-yl)-4-penten-2-ol, having an $[\alpha]^{20}_D$ (neat) of about −15.6°;

g. (+)-(2S,E)-3,3-dimethyl-5-(2',2',3'-trimethyl-3'-cyclopenten-1'-yl)-4-penten-2-ol; and h. (−)-(2R,E)-3,3-dimethyl-5-(2',2',3'-trimethyl-3'-cyclopenten-1'-yl)- 4-penten-2-ol.

It further concerns a method to confer, enhance, improve or modify the odor properties of a perfuming composition or a perfumed article, which method comprises adding to said composition or article a fragrance effective amount of one of said compounds.

Another object of the invention is to provide perfuming compositions or perfumed articles resulting from the above-mentioned method.

In addition, the invention also relates to processes for the preparation of the compounds cited above.

BACKGROUND OF THE INVENTION

The present invention relates to the field of perfumery. It concerns, more particularly, the use of optically active isomers of (E)-3,3-dimethyl- 5-(2,2,3-trimethyl-3-cyclopenten-1-yl)-4-penten-2-ol as perfuming ingredients.

The above-mentioned compound has been described in European patent N° 155 591, wherein its odor is said to be of the sandalwood, balsamic, sweet and milky type. Furthermore, an optically active isomer of said compound, i.e. (−)-(E)-3,3-dimethyl-5-(2',2',3'-trimethyl-3'-cyclopenten-1'-yl)- 4-penten-2-ol, is also described, but no mention of its characteristic odor properties can be found in this reference. In fact, it is quite clear that the specific odor properties of each individual optically active isomer or chiral species went totally undetected at the time, since it is indicated in the document mentioned above that the various diastereomers of each compound described were hardly distinguishable from each other, from an olfactive point of view. On the basis of this document, no advantage would therefore have been expected from the use in perfumery of any one of the optically active isomers in particular. Yet, it has just been surprisingly discovered that in fact some of said isomers are choice perfuming ingredients, while others are less useful for perfumery applications.

DETAILED DESCRIPTION OF THE INVENTION

Thus, one object of the present invention is to provide (+)-(1'S,E)- 3,3-dimethyl-5-(2',2',3'-trimethyl-3'-cyclopenten-1'-yl)-4-penten-2-ol having an $[\alpha]^{20}_D$ (neat) of about +18.3° and (−)-(1'R,E)-3,3-dimethyl-5-(2',2',3 '-trimethyl-3'-cyclopenten-1'-yl)-4-penten-2-ol having an $[\alpha]^{20}_D$ (neat) of about −15.6°.

It has now been established that, unlike what is mentioned in the above-cited prior art document, these optically active isomers of the alcohol mentioned above have a characteristic odor, distinct from each other. Although they both possess a basic sandalwood type odor, the olfactive effect that they impart to the compositions and articles into which they are incorporated is actually quite different. Thus (−)-(1'R,E)-3, 3-dimethyl-5-( 2',2',3'-trimethyl-3'-cyclopenten-1'-yl)-4-penten-2-ol develops a sandalwood note, the character of which is strongly reminiscent of the typical milky odor of sandalwood, while the fragrance imparted by (+)-(1'S,E)-3, 3-dimethyl-5-( 2',2',3'-trimethyl-3'-cyclopenten-1'-yl)-4-penten-2-ol is drier, more woody-cedar and less milky than that of its isomer above-mentioned. The examples presented further on clearly show that these two chiral species can thus be advantageously used, without redundancy, for the preparation of perfuming compositions and perfumed articles, the perfumers preferring one or the other according to the nature of the application and the particular odor connotation that they wish to achieve. Namely, it has been observed that the isomer of (−)-(1'R,E) configuration is particularly appreciated by some perfumers for fine perfumery applications, while the isomer of (+)-(1'S,E) configuration is judged more advantageous for so-called technical perfumery applications, i.e. for perfuming soaps, detergents and a variety of other consummer products, as a result of its enhanced odor intensity and the improved performance of its sandalwood note in these products.

The fact that both these compounds find advantageous use in perfumery is the result of a discovery that we have just made. In fact, each one of them is a mixture ot two diastereomers and it has been surprisingly observed that said diastereomers also have quite distinguishable olfactive behaviours. As a result of its structure, which possesses two chiral centers, (E)-3,3-dimethyl-5-(2,2,3-trimethyl-3-cyclopenten-1-yl)-4-penten-2-ol can assume the form of four optically active isomers, amongst which the isomer of (+)-(1'S,2S,E) configuration has revealed itself as a choice perfuming ingredient. This compound develops a sandalwood note of remarkable strength, wherein the typical milky character is represented at its best and accompanied by a slightly animal note. This isomer turns out to be the determining component, from the point of view of the odor contribution, in (+)-(1'S,E)-3,3-dimethyl-5-(2',2',3'-trimethyl-3'-cyclopenten-1'-yl)- 4-penten-2-ol, since the isomer of (+)-(1'S,2R,E) configuration, the other component, develops a weaker and less characteristic sandalwood note. Curiously, it would seem that it is the chiral center in the lateral chain which is responsible for the odor performance of these compounds, since it has also been established that the isomer of (−)-(1'R,2S,E) configuration possessed an odor superior, both as regards the strength and the character of the sandalwood note, to that of its (−)-(1'R,2R,E) diastereomer, and is in fact responsible for the elegant and much appreciated fragrance of the (−)-(1'R,E)-3,3-dimethyl-5-(2',2',3'-trimethyl-3'-cyclopenten-1'-yl)-4-penten-2-ol cited above.

As is apparent from the examples presented further on, the diastereomers of (+)-(1'S,2S,E) and (−)-(1'R,2S,E) configuration were systematically preferred by the perfumers in the comparative evaluation tests carried out, and the use of these compounds in perfumery is preferred according to the invention. Likewise, the mixtures of these diastereomers, independently of the relative proportions of the two components, turned out to be useful perfuming ingredients according to the invention. Such was the case for example of the mixture containing equal amounts of both components, i.e. (+)-(2S,E)-3,3-dimethyl-5-(2',2',3'-trimethyl-3'-cyclopenten- 1'-yl)-4-penten-2-ol.

As a result of their odor properties, the compounds of the invention can be used for perfuming a wide variety of products, such as perfumes and colognes, soaps, bath and shower gels, shampoos and other hair-care products, cosmetic preparations, body or air deodorants, detergents or fabric softeners, or yet household products. In these applications they can be used either on their own or, as it is more common, in admixture with other perfuming ingredients, solvents or adjuvants of current use in perfumery and which can be easily selected by the skilled person as a function of the desired fragrance effect and the nature of the product to be perfumed.

The concentrations in which the compounds according to the invention can be used to obtain the desired perfuming effects vary in a wide range of values, which, as is well-known, depend on the nature of the product to be perfumed and on the fragrance effect that one wants to achieve, as well as on the nature of the odor perfuming co-ingredients present in a given composition. Thus concentrations of the order of 1 to 5%, or even 10 or 20% by weight of compound according to the invention, relative to the weight of the composition, are quite appropriate whenever said compound is added to a variety of perfuming compositions. Much lower concentrations can be used when applying the compounds of the invention to perfume the various articles cited above.

The mixtures of diastereomers according to the invention such as the (+)-(1'S,E)- and (−)-(1'R,E)-3,3-dimethyl-5-(2',2',3'-trimethyl-3'-cyclopenten-1'-yl)-4-penten-2-ols, were prepared from the appropriate optically active isomers of campholenic aldehyde, following the method described in EP 155 591. Special care was observed in using starting products of high optical purity to ensure that one would obtain the desired final products with at least 97% optical purity. The analytical characters of these compounds were identical to those described in the European patent cited, only the optical rotation angles being different and as indicated hereinafter:

a. (+)-(1'S,E)-3,3-dimethyl-5-(2',2',3'-trimethyl-3'-cyclopenten-1'-yl)-4-penten-2-ol
$[\alpha]_D^{20}$ (neat)=+18.3°
(−)-campholenic aldehyde (starting product)
$[\alpha]_D^{20}$ (neat)=−9.6°
(+)-(1'S,E)-3-methyl-5-(2',2',3'-trimethyl-3'-cyclopenten-1'-yl)-4-penten-2-one (intermediate product)

$[\alpha]_D^{20}$ (neat)=+1.5°
(+)-(1'S,E)-3,3-dimethyl-5-(2',2',3'-trimethyl-3'-cyclopenten-1'-yl)-4-penten-2-one (intermediate product)
$[\alpha]_D^{20}$ (neat)=+26.4°
b. (−)-(1'R,E)-3,3-dimethyl-5-(2',2',3'-trimethyl-3'-cyclopenten-1'-yl)-4-penten-2-ol
$[\alpha]_D^{20}$ (neat)=−15.6°
(−)-(1'R,E)-3,3-dimethyl-5-(2',2',3'-trimethyl-3'-cyclopenten-1'-yl)-4-penten-2-one (intermediate product)
$[\alpha]_D^{20}$=−26.6°; c=1.75, CHCl$_3$ On the other hand, the preparation of the four pure diastereomers of 3,3-dimethyl-5-(2,2,3-trimethyl-3-cyclopenten-1-yl)-4-penten-2-ol, which are novel compounds, as well as their use in perfumery, namely that of the preferred compounds of the invention, are the result of laborious studies, involving original methods. In fact, the preparation of the two diastereomers present in each of the compounds mentioned above proved particularly difficult. It was quite impossible, in particular, to obtain said diastereomers from those compounds through current separation techniques such as gas or liquid phase preparative chromatography, distillation or yet crystallization from selected solvents.

Furthermore, owing to the steric hindrance of the -OH group (due to the presence of the gemdimethyl group) and its small dimension, many well-known and currently used chemical processes of separating diastereomers proved totally inefficient in the present case, both as regards the purity of the desired product and/or the yield in the latter.

It has however been unexpectedly discovered that these diastereomers could be obtained in a pure state and in useful yield via an original process, which comprises treating with an excess of metallic sodium, in diethyl ether, un keto-ether of formula

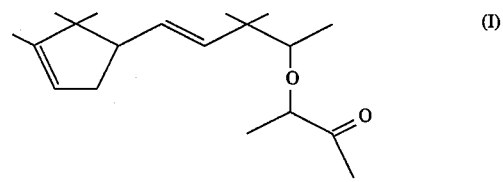

in the form of an appropriate optically active isomer thereof, to obtain the corresponding optically active isomer of 3,3-dimethyl-5-(2,2,3-trimethyl-3-cyclopenten- 1-yl)-4-penten-2-ol.

The reaction which characterises the process of the invention takes place under the conditions described in detail further on. The optically active compounds (I), used as starting products in this process, are novel compounds which can be prepared from (+)-(1'S,E)- and (−)-(1'R,E)-3,3-dimethyl- 5-(2',2',3'-trimethyl-3'-cyclopenten-1'-yl)-4-penten-2-ones, by way of the reactions illustrated in the following scheme for one of these starting products:

SCHEME I

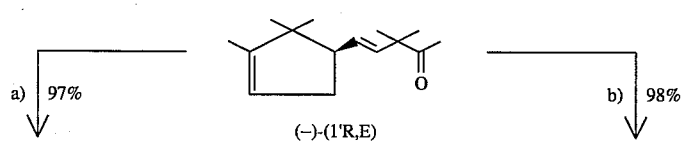

-continued
SCHEME I

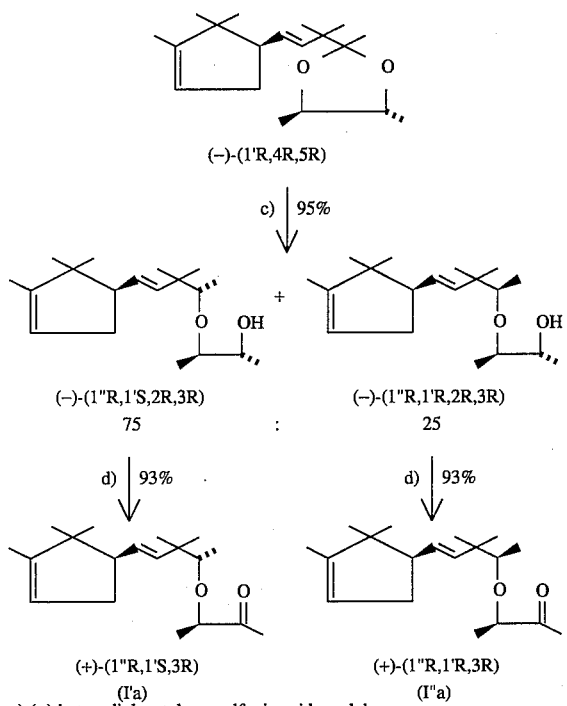
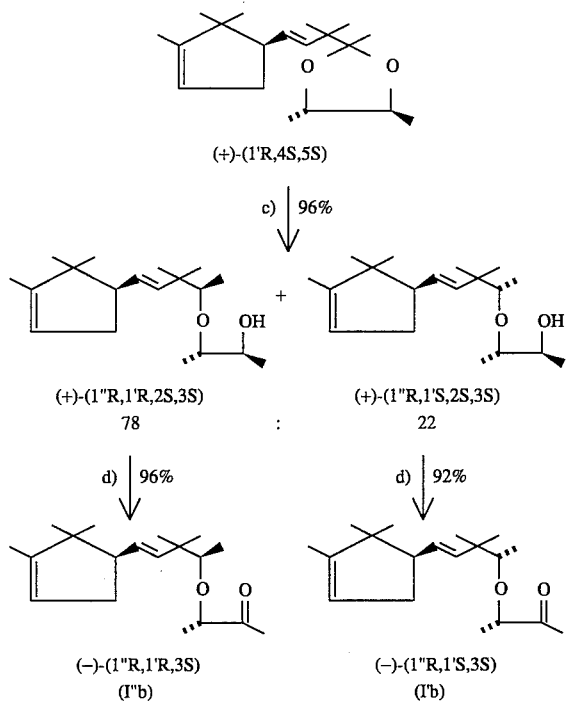

a) (−)-butanediol, p-toluenesulfonic acid, cyclohexane
b) (+)-butanediol, p-toluenesulfonic acid, cyclohexane
c) LiAlH$_4$, AlCl$_3$, ethyl ether
d) PCC (pyridinium chlorochromate), CH$_2$Cl$_2$ The starting ketones are converted into the represented chiral acetals by means of (+) or (−)-butanediol. The subsequent reaction consists in a stereoselective addition of a hydride onto the above-mentioned acetals, to provide the hydroxy-ethers represented, in the form of mixtures of two diastereomers, present in the proportions indicated. These diastereomers are separated by chromatography and then oxidized to give the corresponding keto-ethers. The latter are then converted according to the invention, the compounds of formula (I'a) and (I'b) being precursors of (−)-(1'R,2S,E)-3, 3-dimethyl- 5-(2',2',3'-trimethyl-3'-cyclopenten-1'-yl)-4-penten-2-ol, and the compounds of formula (I"a) and (I"b) being precursors of its (−)-(1'R,2R,E) isomer.

It goes without saying that, if the same reaction sequence is applied to (+)-(1'S,E)-3,3-dimethyl-5-(2',2',3'-trimethyl-3'-cyclopenten-1'-yl)-4 -penten-2-one, one will obtain the keto-ethers which are precursors of the (+)-(1'S,2S,E)- and (+)-(1'S,2R,E)-3,3-dimethyl-5-(2',2',3'-trimethyl- 3'-cyclopenten-1'-yl)-4-penten-2-ols according to the invention.

According to the process of the invention, these four chiral pentenols are obtained with optical purities of at least 90%. If desired, they can be further purified by means of currently used processes, for example, via formation of derivatives whose diastereomers have distinct solubilities in certain solvents and can therefore be separated from one another by crystallisation. One such example is described in detail further on and resorts to the preparation of dinitrobenzoate derivatives. Another alternative used involved the preparation of camphanoate derivatives, the diastereomers of which could then be separated from one another by chromatography. The use of one or the other of these methods depended on the nature of the product to be purified and in particular on the content of said product in the desired isomer, the first of said methods having revealed itself efficient only when the product to be purified was already enriched in the latter.

The absolute configuration of all the chiral products obtained was established by means of the Horeau test [see A. Horeau, Tetrahedron Lett.15, 506 (1961)] and confirmed by chemical correlation [see S. Brooks et al., J. Chem. Soc. Perkin 1, 1974, 2114; J. Chem. Soc. Chem. Comm. 1971, 1359].

The invention also relates to an alternative process for the preparation of the four chiral isomers of 3,3-dimethyl-5-(2, 2,3-trimethyl-3-cyclopenten- 1-yl)-4-penten-2-ol, wherein the diastereomers are obtained from the mixtures of diastereomers described above, i.e. (−)-(1'R,E)- and (+)-(1'S,E)-3,3-dimethyl-5-(2',2',3'-trimethyl-3'-cyclopenten-1'-yl)-4-penten-2-ol, via esterification thereof in the form of an acetate or chloroacetate, subsequent enzymic hydrolysis of the resulting product by means of an appropriate lipase and finally separation of the desired products.

The hydrolysis is carried out at a temperature comprised between 25° and 40° C. and a pH in a range of values of between 5 and 8. Appropriate lipases are commercial enzymes commonly designated as triacyl glycerol acyl hydrolases E.C. 3.1.1.3, for example the Porcine Pancreas Lipases (PPL) sold by Sigma Chem. Co. under the tradenames of Lipase Type VI or Lipase n° L-3126 Type II. Such enzymes are capable of selectively hydrolyzing only one of the diastereomers of the chloroacetate previously formed, leaving the other one unreacted. The two products of the hydrolysis can then be separated by chromatography.

The process of the invention is defined as in the claims and described in detail further on.

The invention will now be described in further detail by way of the following examples, wherein the temperatures are indicated in degrees centigrade and the abbreviations have the usual meaning in the art.

EXAMPLE 1

Preparation of (−)-(1'R,2R,E)-3,3-dimethyl-5-(2',2',3'-trimethyl-3' -cyclopenten-1'-yl)-4-penten-2-ol a. From (−)-(1'R,E)-3,3-dimethyl-5-(2',2',3'-trimethyl-3'-cyclopenten-1'-yl)- 4-penten-2-ol (2R/2S 1:1; $[\alpha]^{20}{}_D$ (neat)= −15.6°).

This compound (26.8 mmole) was esterified by means of ClCH$_2$COCl (2.1 ml, 31.9 mmole), in pyridine (2.1 ml), to give (−)-(1'R,E)-1,2,2-trimethyl-( 2',2',3'-trimethyl-3'-cyclopenten-1'-yl)-3-butenyl chloroacetate ($[\alpha]^{20}{}_D$ (neat)=− 15.8°). The latter was then hydrolysed at 36° by means of 8 g of PPL (Lipase L-3126, Type II; origin: Sigma Chem. Co.), in 400 ml of a 0.1M phosphate solution at pH 7.5. After 24 h, the mixture was extracted with ether, dried over MgSO$_4$ and evaporated. These operations were repeated three times to give 20 g of an oil which was purified by chromatography on SiO$_2$ with cydohexane/ethyl acetate 83:17, to provide 13.8 g of (−)-(1'R,1S,E)-1,2,2-trimethyl-4-(2',2',3'-trimethyl-3'-cyclopenten- 1'-yl)-3-butenyl chloroacetate (unreacted) and 4.75 g of the desired (−)-(1'R,2R,E)-3,3-dimethyl-5-(2',2',3'-trimethyl-3'-cyclopenten-1'-yl)- 4-penten-2-ol ($[\alpha]^{20}{}_D=-25.4°$; c=3.03, CHCl$_3$; diastereomeric excess (d.e.) 90%).

The above-mentioned chloroacetate presented the following analytical characters:

$[\alpha]^{20}{}_D=-16.13°$; c=4.84, CHCl$_3$

IR: 2900, 1760, 1460, 1380, 1360, 1290, 1190, 1110, 1050, 980 cm$^{-1}$

NMR($^1$H,360 MHz): 0.73(s, 3H); 0.95(s, 3H); 1.03(s, 6H); 1.18(d, J=7, 3H); 1.61(q, J=2, 3H); 2.01–2.12(m, 1H); 2.18–2.28(m, 1H); 2.33(q, J=7, 1H); 4.04(s, 1H); 4.84(q, J=7, 1H); 5.23(large s, 1H); 5.41(d, J=16, 1H); 5.48(dd, J=7, 16, 1H) δ ppm NMR($^{13}$C): 12.7(q); 15.2(q); 20.5(q); 23.4(q); 23.9(q); 25.4(q); 35.5(t); 39.8(s); 41.2(t); 48.1(s); 54.3(d); 79.3(d); 121.5(d); 129.9(d); 136.1(d); 148.05(s); 166.9(s) δ ppm MS: 298(M$^+$,14), 204(13), 189(12), 177(37), 135(20), 121(56), 109(74), 91(30), 77(69), 69(100), 55(22), 41(28)

The above-mentioned pentenol (4.44 g, 20 mmole) was further purified by esterification with 3,5-dinitrobenzoyl chloride (6.92 g; 24 mmole) in pyridine (20 ml) and heptane (80 ml) during 5 h, at 25°. After extracting with ether and washing to neutrality, the reaction product was dried and evaporated. It was then chromatographed on SiO$_2$ (eluting agent: cyclohexane/ethyl acetate 97:3) and recrystallised in ethanol at reflux, to give (−)-(1'R,1R,E)-1,2,2-trimethyl-4-(2',2',3'-trimethyl-3'-cyclopenten-1' -yl)-3-butenyl 3,5-dinitrobenzoate with the following analytical characters:

M.p.=79°–80°

$[\alpha]^{20}{}_D=-40.4°$; c=0.83, CHCl$_3$

IR: 3100, 3040, 2980, 1730, 1625, 1545, 1350, 1280, 1180, 1080 cm$^{-1}$

NMR($^1$H,360 MHz): 0.73(s, 3H); 0.94(s, 3H); 1.05(s, 3H); 1.06(s, 3H); 1.34(d, J=7, 3H); 1.60(q, J=2, 3H); 2.01(m, 1H); 2.17(m, 1H); 2.38(q, J=7, 1H); 5.11(q, J=7, 1H); 5.21(large s, 1H); 5.52(m, 2H); 9.12(d, J=2, 2H); 9.22(t, J=2, 1H) δ ppm NMR($^{13}$C): 12.7(q); 15.3(q); 18.45(q); 20.5(q); 23.9(q); 25.4(q); 35.5(t); 40.1(s); 48.15(s); 54.3(d); 80.2(d); 121.4(d); 122.2(d); 129.3(2d); 130.45(d); 134.6(s); 136.0(d); 148.1(s); 148.7(s); 162.0(s) δ ppm

MS: 416(M$^+$,40), 401(10), 195(40), 177(100), 149(23), 109(22), 69(21)

The crystals thus obtained (4.4 g; 10.58 mmole) were saponified by means of 710 mg (12.7 mmole) of KOH and 3 ml of ethanol, the mixture having been taken to reflux for 30 min. After cooling, the mixture was extracted with ether, washed to neutrality with H$_2$O, dried and evaporated. Bulb-to-bulb distillation (100°/4 Pa) provided (−)-(1'R,2R,E)-3, 3-dimethyl-5-(2',2',3' -trimethyl-3'-cyclopenten-1'-yl)-4-penten-2-ol with the following analytical characters:

$[\alpha]^{20}{}_D=-26.6°$; c=4.72, CHCl$_3$; d.e. 94%

NMR($^1$H,360 MHz): 0.73(s, 3H); 0.95(s, 3H); 1.0(s, 3H); 1.01(s, 3H); 1.12(d, J=7, 3H); 1.55(large s, 1H); 1.61(q, J=2, 3H); 2.05–2.13(m, 1H); 2.2– 2.3(m, 1H); 2.38(q, J=7, 1H); 3.49(q, J=7, 1H); 5.23(large s, 1H); 5.39(d, J=16, 1H); 5.5(dd, J=7, 16, 1H) δ ppm NMR($^{13}$C): 12.7(q); 17.4(q); 20.5(q); 22.1(q); 24.0(q); 25.4(q); 35.55(t); 41.0(s); 48.1(s); 54.3(d); 74.2(d); 121.5(d); 130.5(d); 137.5(d); 148.0(s) δ ppm b. From (−)-(1"R,1'R,3S,E)- or (+)-(1"R,1'R,3R,E)-3-[1', 2',2' -trimethyl-4'-(2",2",3"-trimethyl-3"-cyclopenten-1"-yl)-3'-butenyloxy]-2-butanone A suspension of the butanone having (−)-(1"R,1'R,3S,E) configuration (800 mg, 2.74 mmole) and sodium (800 mg; 33.3 atg) in dry ether (10 ml) was stirred for 4days. After filtering on SiO$_2$, evaporation and chromatography, there was obtained (−)-(1'R,2R,E)-3,3-dimethyl-5-(2',2',3'-trimethyl- 3'-cyclopenten-1'-yl)-4-penten-2-ol (yield 49%) with the same characters as indicated above, excepting:

$[\alpha]^{20}{}_D=-22.1°$; c=1.05, CCl$_4$, d.e. 80%

A similar product is obtained when the butanone of (+)-(1"R,1'R,3R,E) configuration is used as starting product. The alcohols thus obtained can be further purified as described under a.

The starting butanones were prepared as follows.

A. (+)-(1'R,4S,5S,E)- and (−)-(1'R,4R,5R,E)-2-[1,1-dimethyl-3-( 2',2',3'-trimethyl-3'-cyclopenten-1'-yl)-2-propenyl] -2,4,5-trimethyl-1,3-dioxolane 485 mg (2.2mole) of (−)-(1'R,E)-3,3-dimethyl-5-(2',2',3'-trimethyl-3' -cyclopenten-1'-yl)-4-penten-2-one ($[\alpha]^{20}{}_D=-26.6°$; c=1.75, CHCl$_3$) and 180 mg of (+)-(2S,3S)-butanediol (2.0 mmole) were taken to reflux in 15 ml of cyclohexane with 10 mg of p-toluenesulfonic acid and a water separator. After 5 h, the reaction mixture was evaporated under vacuum and the residue chromatographed on SiO$_2$ (eluting agent: cyclohexane/ethyl acetate 97:3) to give the dioxolane of (+)-(1'R,4S,5S,E) configuration, which presented the following characters (yield 98%): $[\alpha]^{20}{}_D=+9.0°$; c=1.0, CHCl$_3$ IR: 3040, 3000, 2900, 1470, 1450, 1390, 1250, 1190, 1130, 1110, 1000, 800 cm$^{-1}$ NMR($^1$H,360 MHz): 0.75(s, 3H); 0.94(s, 3H); 1.07(s, 6H); 1.21(d, J=7, 3H); 1.26(d, J=7, 3H); 1.28(s, 3H); 1.61 (d, J=2, 3H); 2.0–2.12(m, 1H); 2.2–2.3(m, 1H); 2.38(q, J=8, 1H); 3.48–3.55(m, 1H); 3.62–3.70(m, 1H); 5.23(large s, 1H); 5.45(dd, J=8, 12, 1H); 5.62(d, J=12, 1H) δ ppm NMR($^{13}$C): 12.7(q); 15.95(q); 17.7(q); 20.5(q); 22.0(q); 22.75(q); 22.9(q); 25.5(q); 35.6(t); 44.65(s); 48.25(s); 54.3(d); 77.8(d); 79.5(d); 112.4(d); 121.6(d); 128.8(d); 137.4(d); 148.15(s) δ ppm

MS: 292(M$^+$, 0), 277(1), 115(100), 73(10), 55(10), 43(42).

Following an identical process but using (−)-(2R,3R)-butanediol (180 mg), there was obtained the dioxolane of (−)-(1'R,4R,5R,E) configuration which had the following characters (yield 97%): $[\alpha]^{20}{}_D=-36.1°$; c=1.2, CHCl$_3$ IR: 3040, 3000, 2900, 1470, 1450, 1390, 1250, 1190, 1130, 1110, 1000, 800 cm$^{-1}$ NMR($^1$H,360 MHz): 0.73(s, 3H); 0.95(s, 3H); 1.05(s, 3H); 1.06(s, 3H); 1.21(d, J=7, 3H); 1.26(d, J=7, 3H); 1.28(s, 6H); 1.62(q, J=2, 3H); 2.01– 2.11(m, 1H); 2.20–2.30(m, 1H); 2.39(q, J=8, 1H); 3.45–3.55(m, 1H); 3.65–3.72(m, 1H); 5.22(large s, 1H); 5.44(dd, J=8, 12, 1H); 5.65(d, J=12; 1H) δ ppm NMR($^{13}$C): 12.7(q); 16.0(q); 17.7(q); 20.5(q); 22.0(q); 22.65(q); 23.0(q); 25.5(q); 35.55(t); 44.65(s); 48.2(s); 54.2(d); 77.8(d); 79.5(d); 112.4(s); 121.6(d); 128.6(d); 137.5(d); 148.1(s) δ ppm

MS: 292(M$^+$,0), 277(1), 115(100), 73(10), 55(10), 43(41).

B. (−)-(1"R,1'S,2R,3R,E)- and (−)-(1"R,1'R,2R,3R,E)-3-[1',2',2'-trimethyl-4'-( 2",2",3"-trimethyl-3"-cyclopenten-1"-yl)-3'-butenyloxy]-2-butanol 390 mg (10.27 mmole) of LiAlH$_4$ in 20 ml of dry ether were cooled to −25°. A solution of (−)-(1'R,4R,5R,E)-2-[1,1-dimethyl-3-(2',2',3' -trimethyl-3'-cyclopenten-1'-yl)-2-propenyl]-2,4,5-trimethyl-1,3-dioxolane (600 mg; 2.05 mmole) and AlCl$_3$ (1370 mg; 10.27 mmole) in 20 ml of ether was added dropwise thereto, under nitrogen and magnetic stirring. After 26 h, the mixture was washed to neutrality with NaHCO$_3$ to provide a mixture of the desired butanols [(−)-(1"R,1'S,2R,3R)/(−)-(1"R,1'R,2R,3R) 3:1]. These compounds were separated by chromatography (SiO$_2$, cyclohexane/ethyl acetate 97:3 to 9:1) to provide the desired compounds with the following characters:

(−)-(1"R,1'S,2R,3R,E) (purity 92%, yield 48%)

[α]$^{20}_D$=−38.8°; c=1.0, CCl$_4$

IR: 3500, 2960, 1460, 1380, 1260, 1100, 980, 790 cm$^{-1}$

NMR($^1$H,360 MHz): 0.73(s, 3H); 0.95(s, 3H); 1.01(s, 6H); 1.08(d, J=7, 3H); 1.09(d, J=7, 3H); 1.23(d, J=7, 3H); 1.61(q, J=2, 3H); 2.07(m, 1H); 2.23(m, 1H); 2.38(q, J=8, 1H); 2.83(d, J=2, 1H, OH); 3.21 (m, 1H); 3.25(m, 1H); 3.52(m, 1H); 5.22(large s, 1H); 5.45(m, 1H); 5.52(d, J=16, 1H) δ ppm NMR($^{13}$C): 12.7(q); 16.9(q); 17.6(q); 18.7(q); 20.5(q); 23.9(q); 24.25(q); 25.4(q); 35.4(t); 41.2(s); 48.0(s); 54.2(d); 72.0(d); 80.6(d); 82.5(d); 121.55(d); 128.7(d); 138.2(d); 148.1(s) δ ppm

MS: 294(M$^+$,0), 205(2), 117(26), 73(100), 55(20)

(−)-(1"R,1'R,2R,3R,E) (purity 95%, yield 17%)

[α]$^{20}_D$=−52.4°; c=0.25, CCl$_4$

IR: 3500, 2960, 1460, 1380, 1260, 1100, 980, 790 cm$^{-1}$

NMR($^1$H,360 MHz): 0.73(s, 3H); 0.93(s, 3H); 1.02(s, 3H); 1.03(s, 3H); 1.06(d, J=7, 3H); 1.08(d, J=7, 3H); 1.14(d, J=7, 3H); 1.61(q, J=2, 3H); 2.06(m, 1H); 2.22(m, 1H); 2.34(m, 1H); 2.78(large s, 1H, OH); 3.20(m, 2H); 3.50(m, 1H); 5.22(large s, 1H); 5.42(m, 2H) δ ppm NMR($^{13}$C): 12.75(q); 14.4(q); 15.5(q); 18.6(q); 20.5(q); 23.0(q); 24.95(q); 25.4(q); 35.65(t); 40.3(s); 48.15(s); 54.4(d); 71.2(d); 76.7(d); 78.6(d); 121.6(d); 128.5(d); 137.9(d); 148.1(s) δ ppm

MS:294(M$^+$,0), 205(2), 117(24), 73(100), 55(20)

C. (+)-(1"R,1'R,2S,3S,E)- and (+)-(1"R,1'S,2S,3S,E)-3-[1',2',2'-trimethyl-4'-( 2",2",3"-trimethyl-3"-cyclopenten-1"-yl)-3'-butenyloxy]-2-butanol Prepared in an analogous manner to that described under B. but using (+)-(1'R,4S,5S,E)-2-[1,1-dimethyl-3-(2',2',3'-trimethyl-3'-cyclopenten-1'-yl)-2-propenyl]-2,4,5-trimethyl-1,3-dioxolane as starting product.

(+)-(1"R,1'R,2S,3S,E) (purity 90%, yield 52%)

[α]$^{20}_D$=+10.4°; c=1.2, CCl$_4$

IR: 3500, 2960, 1460, 1380, 1260, 1100, 980, 790 cm$^{-1}$

NMR($^1$H,360 MHz): 0.73(s, 3H); 0.92(s, 3H); 0.99(s, 3H); 1.02(s, 3H); 1.09(d, J=7, 6H); 1.11(d, J=7, 3H); 1.60(q, J=2, 3H); 2.07(m, 1H); 2.2– 2.4(m, 2H); 2.88(large s, 1H, OH); 3.19(m, 1H); 3.24(m, 1H); 3.52(m, 1H); 5.23(large s, 1H); 5.45(m, 1H) δ ppm NMR($^{13}$C): 12.7(q); 16.75(q); 17.7(q); 18.7(q); 20.5(q); 23.2(q); 24.2(q); 25.4(q); 35.7(t); 41.3(s); 48.2(s); 54.4(d); 72.0(d); 80.8(d); 82.3(d); 121.6(d); 128.9(d); 138.7(d); 148.0(s) δ ppm

MS: 294(M$^+$,0), 117(34), 73(100), 55(16)

(+)-(1"R,1'S,2S,3S) (purity 98%, yield 15%)

[α]$^{20}_D$=+34.7°; c=1.3, CCl$_4$

IR: 3500, 2960, 1460, 1380, 1260, 1100, 980, 790 cm$^{-1}$

NMR($^1$H,360 MHz): 0.74(s, 3H); 0.94(s, 3H); 0.99(s, 3H); 1.00(s, 3H); 1.02(d, J=7, 3H); 1.04(d, J=7, 3H); 1.14(d, J=7, 3H); 1.61 (q, J=2, 3H); 2.08(m, 1H); 2.22(m, 1H); 2.35(m, 1H); 2.79(large s, 1H, OH); 3.19(m, 2H); 3.5(m, 1H); 5.22(large s, 1H); 5.43(m, 2H) δ ppm NMR($^{13}$C): 12.75(q); 14.4(q); 15.45(q); 18.6(q); 20.5(q); 23.4(q); 24.8(q); 25.4(q); 35.6(t); 40.25(s); 48.1 (s); 54.4(d); 71.2(d); 76.5(d); 78.7(d); 121.55(d); 128.45(d); 137.9(d); 148.15(s) δ ppm

MS: 294(M$^+$,0), 117(34), 73(100), 55(14)

D. (−)-(1"R,1'R,3S,E)-, (−)-(1"R,1'S,3S,E)-; (+)-(1"R,1'R,3R,E)- and (+)-(1"R,1'S,3R,E)-3-[1',2',2'-trimethyl-4'-(2",2" ,3"-trimethyl-3" -clopenten-1"-yl)-3'-butenyloxy]-2-butanone These butanones were obtained by oxidation of the appropriate hydroxy-butanols (see Scheme I) described under B. and C., by means of PCC, in dichloromethane. All the products obtained were purified by chromatography on SiO$_2$ (cyclohexane/ethyl acetate 97:3), and obtained with more than 92% yield.

(+)-(1"R,1'S,3R,E) (purity 92%)

[α]$^{20}_D$=+13.3°; c=1.0, CCl$_4$

IR: 2960, 1720, 1460, 1370, 1360, 1110, 980 cm$^{-1}$

NMR($^1$H,360 MHz): 0.72(s, 3H); 0.93(s, 3H); 1.03(s, 6H); 1.06(d, J=7, 3H); 1.27(d, J=7, 3H); 1.61(q, J=2, 3H); 2.05(m, 1H); 2.19(s, 3H); 2.20(m, 1H); 2.35(m, 1H); 3.17(q, J=7, 1H); 3.85(q, J=7, 1H); 5.23(large s, 1H); 5.45(m, 2H) δ ppm NMR($^{13}$C): 12.7(q); 15.4(q); 18.4(q); 20.5(q); 23.2(q); 24.8(q); 25.2(q); 25.4(q); 35.5(0; 40.9(s); 48.1(s); 54.4(d); 80.25(d); 82.2(d); 121.5(d); 128.5(d); 137.95(d); 148.1(s); 211.9(s) δ ppm

MS: 292(M$^+$,0), 115(100), 71(35), 43(16)

(+)-(1"R,1'R,3R,E) (purity 95%)

[α]$^{20}_D$=+35.1°; c=0.2, CCl$_4$

IR: 2960, 1720, 1460, 1370, 1360, 1110, 980 cm$^{-1}$

MS: 292(M$^+$,0), 115(100), 71(26), 43(16)

(−)-(1"R,1'S,3S,E) (purity 90%)

[α]$^{20}_D$=−4.8°; c=1.3, CCl$_4$

IR: 2960, 1720, 1460, 1370, 1360, 1110, 980 cm$^{-1}$

NMR($^1$H,360 MHz): 0.74(s, 3H); 0.94(s, 3H); 1.02(s, 6H); 1.03(d, J=7, 3H); 1.23(d, J=7, 3H); 1.61(q, J=2, 3H); 2.08(m, 1H); 2.19(s, 3H); 2.21(m, 1H); 2.35(m, 1H); 3.21(q, J=7, 1H); 3.79(q, J=7, 3H); 5.23(large s, 1H); 5.45(m, 2H) δ ppm NMR($^{13}$C): 12.7(q); 14.7(q); 16.8(q); 20.5(q); 23.4(q); 24.6(q); 25.4(2q); 29.7(t); 35.6(0; 40.5(s); 48.1(s); 54.45(d); 79.85(d); 81.9(d); 121.5(d); 128.5(d); 137.8(d); 148.15(s); 212.4(s) δ ppm

MS: 292(M⁺,0), 115(100), 71(30), 43(13)

(−)-(1″R,1′R,3S,E) (purity 98%)

$[\alpha]^{20}_D = -37.5°$; c=1.6, CCl$_4$

IR: 2960, 1720, 1460, 1370, 1360, 1110, 980 cm$^{-1}$

NMR($^1$H, 360 MHz): 0.73(s, 3H); 0.93(s, 3H); 1.01(s, 3H); 1.02(s, 3H); 1.06(d, J=7, 3H); 1.26(d, J=7, 3H); 1.61(q, J=7, 3H); 2.07(m, 1H); 2.21(s, 3H); 2.23(m, 1H); 2.35(m, 1H); 3.18(q, J=7, 1H); 3.83(q, J=7, 1H); 5.22(large s, 1H); 5.43(m, 2H) δ ppm NMR($^{13}$C): 12.7(q); 15.45(q); 18.4(q); 20.5(q); 23.2(q); 24.5(q); 25.3(q); 25.4(q); 35.6(t); 40.95(s); 48.2(s); 54.4(d); 80.4(d); 82.1 (d); 121.5(d); 128.65(d); 138.05(d); 148.1(s); 211.9(s) δ ppm

MS: 292(M⁺,0), 115(100), 71(42), 55(12), 43(20)

EXAMPLE 2

Preparation of (−)-(1′R,2S,E)-3,3-dimethyl-5-(2′,2′,3′-trimethyl-3′-cyclopenten- 1′-yl)-4-penten-2-ol a. From (−)-(1′R,E)-3,3-dimethyl-5-(2′,2′,3′-trimethyl-3′-cyclopenten-1′-yl)- 4-penten-2-ol The unreacted chloroacetate obtained according to Example 1a. (11.7 mmole) was saponified by means of KOH (14.3 mmole) in ethanol (10 ml) at reflux, during 30 min. After extracting with ether, the desired alcohol was obtained ($[\alpha]^{20}_D = -7.17°$; c=3.9, CHCl$_3$).

This product was purified following the process described in example 1a., via the (+)-(1′R,1S,E)-1,2,2-trimethyl-4-(2′,2′,3′-trimethyl-3′-cyclopenten- 1′-yl)-3-butenyl · 3,5-dinitrobenzoate, which, upon recrystallisation from ethanol at −20° provided a product with the following characteristics:

$[\alpha]^{20}_D = +5.75°$; c=2,44, CHCl$_3$

IR: 3100, 3040, 2980, 1730, 1625, 1545, 1350, 1280, 1180, 1080 cm$^{-1}$

NMR($^1$H, 360 MHz): 0.69(s, 3H); 0.90(s, 3H); 1.13(s, 6H); 1.34(d, J=7, 3H); 1.59(q, J=2, 3H); 2.05–2.15(m, 1H); 2.22–2.30(m, 1H); 2.39(q, J=7, 1H); 5.12(q, J=7, 1H); 5.23(large s, 1H); 5.52(m, 2H); 9.12(d, J=2, 2H); 9.22(t, J=2, 1H) δ ppm NMR($^{13}$C): 12.7(q); 15.35(q); 20.5(q); 23.9(2q); 25.35(q); 35.6(t); 40.0(s); 48.1(s); 54.4(d); 80.2(d); 121.5(d); 122.2(d); 129.3(2d); 130.5(d); 134.6(s); 135.9(d); 148.0(s); 148.7(s); 162.0(s) δ ppm Saponification of this product provided (−)-(1′R,2S,E)-3,3-dimethyl-5-( 2′,2′,3′-trimethyl-3′-cyclopenten-1′-yl)-4-penten-2-ol with the following characteristics:

$[\alpha]^{20}_D$ (pur)=−6.3°; d.e. 94%

NMR($^1$H, 360 MHz): 0.73(s, 3H); 0.95(s, 3H); 1.00(s, 3H); 1.01(s, 3H); 1.12(d, J=7, 3H); 1.5(d, J=5, 1H); 1.61(q, J=2, 3H); 2.05–2.13(m, 1H); 2.2–2.3(m, 1H); 2.38(q, J=7, 1H); 3.49(q, d, J=5, 7, 1H); 5.23(large s, 1H); 5.41(d, J=16, 1H); 5.5(dd, J=7, 16, 1H) δ ppm NMR($^{13}$C): 12.7(q); 17.45(q); 20.6(q); 22.2(q); 24.1(q); 25.5(q); 35.55(t); 40.9(s); 48.1(s); 54.4(d); 74.3(d); 121.5(d); 130.5(d); 137.3(d); 148.0(s) δ ppm b. From (+)-(1″R,1′S,3R)-ou (−)-(1″R,1′S,3S)-3-[ 1′,2′,2′-trimethyl-4′-(2″,2″,3″-trimethyl- 3″-cyclopenten-1″-yl)-3′-butenyloxy]-2-butanone It was operated as described in example 1b. The above-mentioned (+)-(1″R,1′S,3R)-butanone provided the desired product with $[\alpha]^{20}_D = -8.0°$; c=0.5, CCl$_4$, 92% diastereomeric purity, and the (−)-(1″R,1′S,3S)-butanone gave the alcohol having $[\alpha]^{20}_D = -10.0°$; c=0.5, CCl$_4$. The two starting butanones were obtained as described in example 1b. A–D.

EXAMPLE 3

Preparation of (+)-(1′S,2R,E)-3,3-dimethyl-5-(2′,2′,3′-trimethyl-3′ -cyclopenten-1′-yl)-4-penten-2-ol a. From (+)-(1′S,E)-3,3-dimethyl-5-(2′,2′,3′-trimethyl-3′-cyclopenten-1′-yl)- 4-penten-2-ol (2R/2S 1:1; $[\alpha]^{20}_D$ (neat)= +18.6°)

The procedure was as described in example 1a. but using (+)-(1′S,E)-1,2,2 -trimethyl-(2′,2′,3′-trimethyl-3′-cyclopenten-1′-yl)-3-butenyl chloroacetate ($[\alpha]^{20}_D$ (neat)=+ 18.6°; 5 g, 16.7 mmole; obtained by esterification of the above-mentioned pentenol), 5 g of PPL (Lipase L-3126, Type II; origin: Sigma Chem. Co.) and 5 g de tert-butanol. Chromatography (SiO$_2$; cyclohexane/ethyl acetate 98:2) of the obtained product provided the (+)-(1′S,1S,E)-1,2,2-trimethyl-4-(2′,2′,3′-trimethyl-3′cyclopenten-1′ -yl)-3-butenyl, unreacted, with the following characters:

$[\alpha]^{20}_D = +14.4°$; c=2,75, CCl$_4$

IR: 2900, 1760, 1460, 1380, 1360, 1290, 1190, 1110, 1050, 980 cm$^{-1}$

NMR($^1$H, 360 MHz): 0.73(s, 3H); 0.94(s, 3H); 1.02(s, 3H); 1.03(s, 3H); 1.18(d, J=7, 3H); 1.61(q, J=2, 3H); 2.0–2.1(m, 1H); 2.2–2.3(m, 1H); 2.33(q, J=7, 1H); 4.03(s, 2H); 4.84(q, J=7, 1H); 5.23(large s, 1H); 5.39(d, J=16, 1H); 5.48(dd, J=7, 16, 1H) δ ppm NMR($^{13}$C): 12.7(q); 15.2(q); 20.5(q); 23.2(q); 23.9(q); 25.4(q); 35.6(t); 39.8(s); 41.2(t); 48.2(s); 54.3(d); 79.2(d); 121.5(d); 130.0(d); 136.2(d); 148.1(s); 166.9(s) δ ppm MS: 298(M⁺,14), 204(13), 189(12), 177(37), 135(20), 121 (56), 109(74), 91(30), 77(69), 69(100), 55(22), 41(28) as well as the desired pentenol (after elution of the chloroacetate, the gradient of the solvent was varied to 96:4, 92:8 and finally 9:1) with $[\alpha]^{20}_D = +6.15°$; c=1,22, CCl$_4$; d.e. 94%.

The other analytical characters of the final product were identical to those of its (−)-(1′R,2S,E) enantiomer (example 2).

b. From (−)-(1″S,1′R,3R)- or (+)-(1″S,1′R,3S)-3 -[1′,2′,2′-trimethyl-4′-(2″,2″,3″-trimethyl-3″-cyclopenten-1″-yl)-3′-butenyloxy]-2-butanone It was operated in a similar manner to that described in example 1b., the above-mentioned starting butanones having been obtained from (+)-(1′S,E)-3,3-dimethyl-5-(2′,2′,3′-trimethyl-3′-cyclopenten-1′-yl)-4-penten-2-one ($[\alpha]^{20}_D$ (neat)=+26.4°; see further up) in a manner analogous to that described in example 1b. A–D.

EXAMPLE 4

Preparation of (+)-(1′S,2S,E )-3,3-dimethyl-5-(2′,2′,3′-trimethyl-3′-cyclopenten-1′-yl)-4-penten-2-ol a. From (+)-(1′S,E)-3,3-dimethyl-5-(2′,2′,3′-trimethyl-3′-cyclopenten-1′-yl)4 -penten-2-ol (2R/2S 1:1; $[\alpha]^{20}_D$ (neat)=+18.6°)

The (+)-(1′S,1S,E)-1,2,2-trimethyl-4-(2′,2′,3′-trimethyl-3′-cyclopenten-1′-yl)-3-butenyl chloroacetate (2.7 g, 9.0 mmole; see example 3a.) was saponified with NaOH (400 mg; 10 mmole) in 10 ml of an ethanol/water 4:1 mixture, at reflux, during 30 min. After evaporating under vacuum, extracting with ether, washing to neutrality with water, drying over MgSO$_4$ and evaporating, there was obtained the desired product ($[\alpha]^{20}_D = +22.0°$; c=1.02, CCl$_4$).

This product was then purified as described in example 1a., via the (+)-(1'S,1S,E)-1,2,2-trimethyl-4-(2',2',3'-trimethyl-3'-cyclopenten-1'-yl)-3-butenyl 3,5-dinitrobenzoate which had identical analytical characters to those of its enantiomer described in example 1a., excepting $[\alpha]^{20}_D = +40.8°$; c=1.08, $CCl_4$ This product (0.7 g; 1.68 mmole) was then saponified with NaOH (74 mg; 1.85 mmole) in 5 ml of ethanol/water 4:1. After evaporation, extraction with ether, washing to neutrality with water, drying over $MgSO_4$ and evaporating to dry, there was obtained the (+)-(1'S,2S,E)-3,3-dimethyl-5-( 2',2',3'-trimethyl-3'-cyclopenten-1'-yl)-4-penten-2-ol with $[\alpha]^{20}_D = +26.9°$; c=1.3, $CHCl_3$; d.e. 94%.

The other analytical characters were identical to those of its enantiomer (−)-(1'R,2R) described in example 1.

b. From (−)-(1"S,1'S,3R)- or (+)-(1"S,1'S,3S)-3-[ 1',2',2'-trimethyl-4'-(2",2",3"-trimethyl-3"-cyclopenten-1"-yl)-3'-butenyloxy]-2-butanone Following the procedure described in example 1b., the above-mentioned starting butanones having been obtained from (+)-(1'S,E)-3,3-dimethyl-5-( 2',2',3'-trimethyl-3'-cyclopenten-1'-yl)-4-penten-2-one ($[\alpha]^{20}_D$ (neat)= +26.4°; see above) in a manner analogous to that described in example 1b. A–D.

EXAMPLE 5

Comparative test on smelling strip

The four diastereomers of 3,3-dimethyl-5-(2,2,3-trimethyl-3-cyclopenten-1 -yl)-4-penten-2-ol were evaluated on a blind test on smelling strip by a panel of nine expert perfumers.

The smelling strips were dipped into 10% solutions in dipropyleneglycol (DIPG) of each of the four compounds, such as to impregnate a zone of 1 cm length on the strip. The perfumers were then asked to smell the four strips and to evaluate their odor with regard to the strength and quality of the sandalwood note.

The perfumers were unanimous in their preference for the strip which carried (+)-(1'S,2S,E)-3,3-dimethyl-5-(2',2',3'-trimethyl-3'-cyclopenten-1'-yl)-4-penten-2-ol, whose sandalwood odor was judged remarkably powerful and elegant, with a prized sandalwood milky character. The strip which had been dipped in (−)-(1'R,2S,E)-3,3-dimethyl-5-(2',2',3'-trimethyl-3' -cyclopenten-1'-yl)-4-penten-2-ol was classed in second place by 5 out of 8 perfumers, its sandalwood note having been judged weaker than that of its diastereomer above-mentioned but still very powerful, while the other 3 perfumers preferred the strip carrying (+)-(1'S,2R,E)-3,3-dimethyl-5-(2',2',3'-trimethyl-3'-cyclopenten-1'-yl)-4-penten-2-ol. According to the 8 perfumers, the strip containing (−)-(1'R,2R,E)-3,3-dimethyl-5-(2',2',3'-trimethyl-3'-cyclopenten-1'-yl)-4-penten-2-ol was the least interesting, its odor being less sandalwood-like and less characteristic than that of the other three strips. The ninth perfumer, who generally has some anosmia to the sandalwood notes, could only smell the first strip mentioned.

EXAMPLE 6

Comparative test on smelling strip. The (−)-(1R',E)- and (+)-(1'R,E)-3,3-dimethyl-5-(2',2',3'-trimethyl-3'-cyclopenten-1'-yl)-4-penten-2-ols according to the invention, in 10% solution in dipropylene glycol (DIPG), were evaluated on smelling strip, on a blind test, by a panel of 9 expert perfumers. Six amongst them preferred the odor of the smelling strip impregnated with the solution of (−)-(1'R,E)-3,3 -dimethyl-5-(2',2',3'-trimethyl-3'-cyclopenten-1'-yl)-4-penten-2-ol, finding it strongly sandalwood-like, sweet and milky, more elegant and with more finesse than the odor of the strip which carried the solution of (+)-(1"S,E)- 3,3-dimethyl-5-(2',2',3'-trimethyl-3'-cyclopenten-1'-yl)-4-penten-2-ol.

According to the perfumers' unanimous opinion, however, the latter smelling strip developed a much stronger sandalwood odor, although less milky, drier and more woody-cedar.

These effects were even more noticeable when the (+)-(1"S,2S,E)- and (−)-(1'R,2S,E)-3,3-dimethyl-5-(2',2',3' -trimethyl-3'-cyclopenten-1'-yl)-4 -penten-2-ols were compared with each other on a blind test.

EXAMPLE 7

Perfuming composition

A base perfuming composition, intended for a feminine type perfume, was prepared by admixing the following ingredients:

| Ingredients | Parts by weight |
| --- | --- |
| Benzyl acetate | 60 |
| Geranyl acetate | 10 |
| Styrallyl acetate | 20 |
| Hexylcinnamic aldehyde | 90 |
| 10% *Amyl allyl glycolate | 120 |
| 10% *Ambrox ® DL[1] | 20 |
| Bergamot essential oil | 500 |
| Lemon essential oil | 40 |
| Citronellol | 60 |
| Coumarine | 135 |
| Dihydromyrcenol[2] | 15 |
| Galaxolide ® 50[3] | 95 |
| Hedione ®[4] | 730 |
| 10% *Indol | 15 |
| Isoeugenol | 20 |
| Jasmin absolute | 80 |
| α-Methylionone | 540 |
| Muscone | 90 |
| 1% *Methyl octynecarbonate | 30 |
| 1% *p-Cresol | 80 |
| Phenethylol | 40 |
| Pimento berries essential oil | 30 |
| Benzyl salicylate | 100 |
| Pipol salicylate | 35 |
| Sandalwood essential oil | 920 |
| Undecalactone | 10 |
| 10% *Vanilline | 95 |
| Ylang essential oil | 160 |
| Total | 4140 |

*in DIPG
[1] tetramethyl-perhydronaphthofuran; origin: Firmenich SA, Geneva, Switzerland
[2] 2,6-dimethyl-7-octen-2-ol; origin: IFF Inc., USA
[3] 1,3,4,6,7,8-hexahydro-4,6,6,7,8,8-hexamethyl-cyclopenta[γ]isochromene; origin: IFF Inc., USA
[4] methyl dihydrojasmonate; origin: Firmenich SA, Geneva, Switzerland To this base composition of the woody, oriental type, there were added respectively 100 parts by weight of (+)-(1'S,E)-3,3-dimethyl-5-(2',2',3' -trimethyl-3'-cyclopenten-1'-yl)-4-penten-2-ol to prepare a novel composition A and 200 parts by weight of (−)-(1'R,E)-3,3-dimethyl-5-(2',2',3'-trimethyl-3'-cyclopenten-1'-yl)-4-penten-2-ol to obtain a novel composition B. These two compositions were then evaluated on a blind test by a panel of 9 expert perfumers. The opinion of the latter was divided, six having preferred composition A for its enhanced impact and three having chosen composition B, the odor note of which they judged more elegant. An even more pronounced division of opinions was observed when two compositions, prepared by adding to the base composition the same amount, i.e. 100 parts by weight, of each of the above-mentioned isomers, were evaluated on a blind test. While all the perfumers were in agreement as regards the strength of the odor of the composition containing isomer (+)-(1'S,E), which they found clearly superior to that of the composition containing isomer (−)-(1'R,E), they judged the odor character of the two compositions far too distinct to be able to indicate a preference for one or the other. In their opinion, the first composition developed a less fine sandalwood odor, but with a more pronounced woody-cedar character and a stronger impact, rendering it particularly useful for certain types of technical applications requiring a better price/performance ratio. As regards the second composition, it developed a very elegant sweet, milky fragrance, particularly advantageous for the preparation of perfumes with oriental character.

The olfactive effects described above were even more apparent when the (−)-(1'R,E) diastereomer mixture was replaced by one of its components, i.e. (−)-(1'R,2S,E)-3,3-dimethyl-5-(2',2',3' -trimethyl-3'-cyclopenten-1'-yl)-4-penten-2-ol.

Likewise, the addition of (+)-(1'S,2S,E)-3,3-dimethyl-5-(2',2',3'-trimethyl-3'-cyclopenten-1'-yl)-4-penten-2-ol to the base composition resulted in an enhanced strength of its odor, relative to the odor of the composition which contained the (+)-(1'S,E) mixture of diastereomers.

What we claim is:

1. A compound chosen in the group consisting of:
   a. (+)-(1'S,2R,E)-3,3-dimethyl-5-(2',2',3 '-trimethyl-3'-cyclopenten-1'-yl)-4-penten-2-ol;
   b. (+)-(1'S,2S,E)-3,3-dimethyl-5-(2',2',3 '-trimethyl-3'-cyclopenten-1'-yl) -4-penten-2-ol;
   c. (−)-(1'R,2R,E)-3,3-dimethyl-5-(2',2',3 '-trimethyl-3'-cyclopenten-1'-yl)-4-penten-2-ol;
   d. (−)-(1'R,2S,E)-3,3-dimethyl-5-(2',2',3 '-trimethyl-3'-cyclopenten-1'-yl)-4-penten-2-ol;
   e. (+)-(2S,E)-3,3-dimethyl-5-(2',2',3'-trimethyl-3'-cyclopenten-1'-yl)-4-penten-2-ol; and
   f. (−)-(2R,E)-3,3-dimethyl-5-(2',2',3'-trimethyl-3'-cyclopenten-1'-yl)-4-penten-2-ol.

2. A method to confer, enhance, improve or modify the odor properties of a perfuming composition or a perfumed article, which method comprises adding to said composition or article a fragrance effective amount of a compound according to claim 1.

3. A perfuming composition or a perfumed article containing as an active ingredient a compound according to claim 1.

4. The perfumed article of claim 3, in the form of a perfume or a cologne, a soap, a bath or shower gel, a cosmetic preparation, a shampoo, a body or ambient air deodorant, a detergent or a fabric softener, or a household product.

5. A method to confer, enhance, improve or modify the sandalwood-milky type odor character of a perfuming composition or a perfumed article, which method comprises adding to said composition or article a fragrance effective amount of (−)-(1'R,E)-3,3-dimethyl-5-(2',2',3'-trimethyl-3'-cyclopenten-1'-yl)-4-penten-2-ol.

6. A method to confer, enhance, improve or modify the sandalwood-woody-cedar type odor character of a perfuming composition or a perfumed article, which method comprises adding to said composition or article a fragrance effective amount of (+)-(1'S,E)-3,3-dimethyl-5 -(2',2',3'-trimethyl-3'-cyclopenten-1'-yl)-4-penten-2-ol.

7. A compound of formula (I)

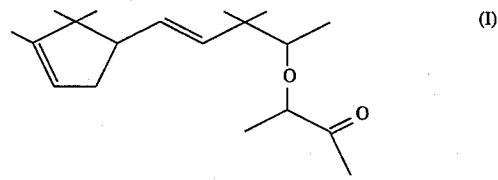

(I)

in racemic or optically active form.

8. The perfuming composition or perfumed article resulting from the method according to claim 5.

9. The perfuming composition or perfumed article resulting from the method according to claim 6.

10. The method of claim 2 wherein the concentration of the active perfuming ingredient is between about 1 and 20% by weight of the composition or article.

11. The perfuming composition or perfumed article or claim 3 wherein the concentration of the active perfuming ingredient is between about 1 and 20% by weight of the composition or article.

12. The method of claim 5 wherein the concentration of the active perfuming ingredient is between about 1 and 20% by weight of the composition or article.

13. The method of claim 6 wherein the concentration of the active perfuming ingredient is between about 1 and 20% by weight of the composition or article.

14. The perfuming composition or perfumed article or claim 8 wherein the concentration of the active perfuming ingredient is between about 1 and 20% by weight of the composition or article.

15. The perfuming composition or perfumed article or claim 9 wherein the concentration of the active perfuming ingredient is between about 1 and 20% by weight of the composition or article.

* * * * *